United States Patent [19]

Akimoto et al.

[11] Patent Number: 5,354,754
[45] Date of Patent: Oct. 11, 1994

[54] PYRROLOPYRIMIDINES, THEIR PRODUCTION AND USE

[75] Inventors: Hiroshi Akimoto, Kobe; Takenori Hitaka, Takarazuka, both of Japan

[73] Assignee: Takeda Chemical Industries, Ltd., Osaka, Japan

[21] Appl. No.: 46,917

[22] Filed: Apr. 14, 1993

Related U.S. Application Data

[63] Continuation of Ser. No. 585,950, Sep. 21, 1990, abandoned.

[30] Foreign Application Priority Data

Sep. 21, 1989 [JP] Japan .................. 1-245998

[51] Int. Cl.$^5$ .................. A61K 31/505; C07D 487/04
[52] U.S. Cl. .................. 514/258; 544/250
[58] Field of Search .................. 514/258, 280

[56] References Cited

U.S. PATENT DOCUMENTS

| | | | |
|---|---|---|---|
| 4,946,846 | 8/1990 | Nomura et al. | 544/280 |
| 4,997,838 | 3/1991 | Akimoto et al. | 514/258 |
| 5,028,608 | 7/1991 | Taylor et al. | 514/258 |

FOREIGN PATENT DOCUMENTS

| | | |
|---|---|---|
| 0079447 | 9/1982 | European Pat. Off. . |
| 0314280 | 9/1988 | European Pat. Off. . |
| 0343801 | 5/1989 | European Pat. Off. . |

OTHER PUBLICATIONS

John M. Venditti in "Cancer Treatment Report" vol. 67, 767–772 (1983).
Experimental Evaluation of Antitumor Drugs in the U.S.A. and U.S.S.R. and Clinical Correlations, p. 34.
Journal of Medicinal Chemistry, 34, 555–560, 1991, Miwa et al.
Journal of Medicinal Chem., vol. 13, 1970, Weinstock et al., "Folic Acid Analogs, II", pp. 995–997, 1970.
Journal of Medicinal Chem., vol. 28, 1985, Taylor et al., "Synthesis of the Antileukemic Agents 5,10-Dideazaaminopterin and 5,10-Dideaza-5,6,7,8-Tetrahydroaminopterin", pp. 914–921; 1985.

*Primary Examiner*—Mukund J. Shaw
*Assistant Examiner*—Y. N. Gupta
*Attorney, Agent, or Firm*—Wegner, Cantor, Mueller & Player

[57] ABSTRACT

A compound of the formula (I):

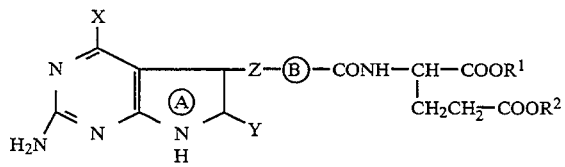

wherein the ring Ⓐ is a pyrrole ring which may be hydrogenated, X is an amino group, a hydroxyl group or a mercapto group, Y is a hydrogen atom or a hydroxyl group, —COOR$^1$ and —COOR$^2$ may be the same or different and are a carboxyl group which may be esterified, —Ⓑ— is a divalent heterocyclic group or a lower alkylene group each of which may be substituted, and Z is a straight C$_{2-4}$ divalent group which may be substituted, or its salt, a method for the production of the same and an antitumor agent containing the same.

5 Claims, No Drawings

PYRROLOPYRIMIDINES, THEIR PRODUCTION AND USE

This application is a continuation of U.S. application Ser. No. 07/585,950 filed Sep. 21, 1990 now abandoned.

BACKGROUND OF THE INVENTION

1. Field of the Invention

This invention relates to novel pyrrolo[2,3-d]pyrimidine derivatives which are useful as antitumor agents.

2. Prior Art

Folic acid is a carrier of a C1 unit in a living body, derived from formic acid or formaldehyde, acting as a coenzyme in various enzymatic reactions such as those in biosynthesis of nucleic acid, in metabolism of amino acids and peptides and in generation of methane. Particularly in the biosynthesis of nucleic acid, folic acid is essential for formylation in the two pathways, i.e. the purine synthetic pathway and the thymidine synthetic pathway. Usually folic acid is required to be transformed into its activated coenzyme form by reduction in two steps before it becomes biologically active.

Amethopterin (methotrexate; MTX) and related compounds are known to inhibit the reduction from dihydrofolic acid to tetrahydrofolic acid by coupling strongly with the dominant enzyme in the second step (dihydrofolic acid reductase). These drugs have been developed as antitumor drugs because they may disturb the DNA synthesis and consequently cause cell death, and are currently regarded as of major clinical importance.

On the other hand, a novel tetrahydroaminopterin antitumor agent (5,10-dideaza-5,6,7,8-tetrahydroaminopterin: DDATHF) has been reported which, unlike the drugs described above, does not inhibit dihydrofolic acid reductase and the main mechanism of which consists in inhibition of glycinamide ribonucleotide transformylase required in the initial stage of purine biosynthesis [Journal of Medicinal Chemistry, 28, 914(1985)].

With regard to the treatment of cancer, it is now strongly expected to develop a new drug which possesses an excellent effect based on a novel mechanism and exhibits a highly selective toxicity against cancer cells. An antitumor agent which mainly antagonizes folic acid, namely, MTX is now widely used in a clinical field, but it is not sufficient due to its relatively high toxicity and insufficient effect on solid tumors. And further, increase of resistance against this type of drug is a big problem.

Thus, some new series of compounds as antitumor agents have been proposed [see European Patent Application No. 0 334 636 (pyrrolopyrimidine derivatives), U.S. Pat. Nos. 4,532,241 and 4,684,653 (Pyridopyrimidine derivatives)] and European Patent Application No. 901110131.1.

SUMMARY OF THE INVENTION

Pyrollo[2,3-d]pyrimidine derivatives, which are not pteridine compounds, exhibit a highly selective toxicity against a variety of tumor cells and also possess an excellent antitumor activity on MTX resistant cells. The present invention relates to (1) a compound of the formula(I)

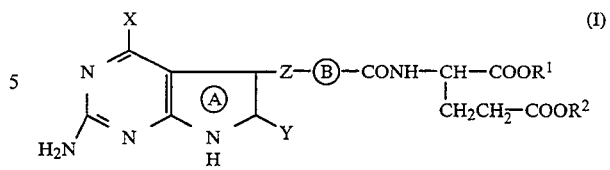

wherein the ring (A) is a pyrrole ring which may be hydrogenated, X is an amino group, a hydroxyl group or a mercapto group, Y is a hydrogen atom or a hydroxyl group, $-COOR^1$ and $-COOR^2$ are the same or different and are a carboxy group which may be esterified, —(B)— is a divalent heterocyclic group or a lower alkylene group each of which may be substituted, and Z is a straightchain divalent group having 2 to 4 carbon atoms which may be substituted, or its salt;

(2) a process for preparing a compound of the above formula (I) or its salt, which comprises reacting a compound of the formula(II)

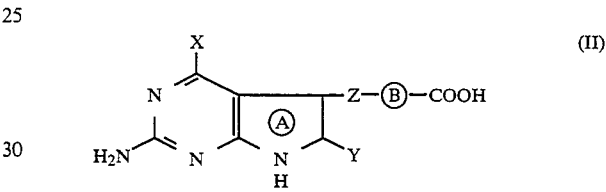

wherein the ring (A), X, Y, —(B)— and Z have the same meanings as above, or its salt or reactive derivative at the carboxy group, with a compound of the general formula(III)

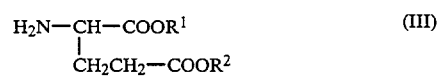

wherein $-COOR^1$ and $-COOR^2$ have the same meanings as above; or its salt;

(3) an antitumor agent containing a compound of the formula (I) or its salt; and (4) a compound of the formula(IV)

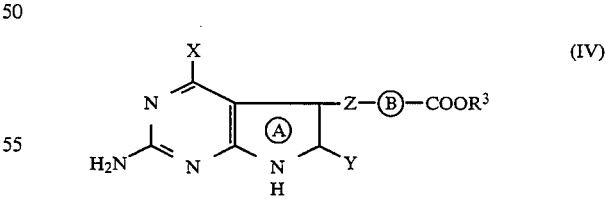

wherein the ring (A), X, Y, —(B)— and Z have the same meanings as above, and $-COOR^3$ is a carboxyl group which may be esterified, or its salt.

In case where X is a hydroxyl or mercapto group and Y is a hydroxyl group in the above formulae, the compounds (I), (II) and (IV) may exist as an equilibrium mixture of tautomers thereof.

Partial structures of the tautomers and their equilibrium state are shown in the following.

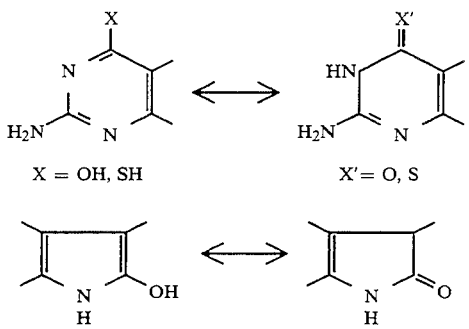

Though these compounds are shown with the hydroxy type and mercapto type and nomenclatures corresponding thereto are applied throughout this specification only for convenience sake, their tautomers, namely, oxo compounds and thioxo compounds are also to be included in the scope of this invention.

Though plural asymmetric centers may exist in the compounds (I) of this invention, the absolute configuration at the asymmetric carbon atom in the side chain derived from glutamic acid is S (L) and the absolute configuration at asymmetric carbon atom(s) in the other cases may be S, R or a mixture of RS. In such case, plural diastereoisomers exist, but they can be easily separated by a conventional method for separation or purification, if necessary. All of the diastereoisomers which can be separated are included in the scope of this invention.

PREFERRED EMBODIMENTS OF THE INVENTION

The pyrrole ring which may be hydrogenated shown by the ring Ⓐ in the above formulae is, for example, a pyrrole or pyrroline ring.

In the above formulae, Z means a divalent group comprising straight chain 2 to 4 carbon atoms (specifically, comprising straight chain 2 to 4 carbon atoms and 0 to 8 hydrogen atoms), and such divalent groups are, for example, $C_{2-4}$ alkylenes such as ethylene, trimethylene and tetramethylene, $C_{2-4}$ alkenylenes such as vinylene, propenylene, 1- or 2-butenylene and butadienylene, or $C_{2-4}$ alkynylenes such as ethynylene, 1- or 2-propynylene and 1- or 2-butynylene, etc. The divalent group represented by Z may have 1 or 2 substituents, such as a $C_{1-3}$ alkyl (e.g., methyl, ethyl, propyl or iso-propyl), a $C_{2-3}$ alkenyl (e.g., vinyl, 1-methylvinyl, 1-propenyl, allyl or allenyl), a $C_{2-3}$ alkynyl (e.g., ethynyl, 1-propynyl or propargyl), cyclopropyl, fluoro, hydroxy, oxo, methoxy, dimethylamino, diethylamino, trifluoromethyl, formyl, hydroxymethyl, 2-hydroxyethyl, methoxymethyl, 2-methoxyethyl, or the like.

Examples of the carboxy groups which may be esterified shown by —COOR$^1$, —COOR$^2$ and —COOR$^3$ are carboxy groups which may be esterified by a $C_{1-5}$ lower alkyl group, a benzyl group which may be substituted, a phenyl group which may be substituted or the like. The lower alkyl group may be, for example, methyl, ethyl, propyl, iso-propyl, n-butyl, iso-butyl, sec-butyl, tert-butyl, n-pentyl, iso-pentyl, sec-pentyl, neo-pentyl, tert-pentyl, etc., and the benzyl group which may be substituted is, for example, benzyl, nitrobenzyl, methoxybenzyl, etc., and the phenyl group which may be substituted is, for example, phenyl, nitrophenyl, methoxyphenyl, etc.

The divalent heterocyclic group from the divalent heterocyclic group or lower alkylene group each of which may be substituted as represented by —Ⓑ—, may be a residue of a 5 or 6-membered ring which is not ionized, and the lower alkylene group may be a $C_{2-4}$ alkylene group. The 5- membered heterocyclic group is, for example, thiophen-(2,4-, 2,5- or 3,4-)ylene, furan-(2,4-, 2,5- or 3,4-)ylene, pyrrol-(1,3-, 2,4-, 2,5- or 3,4-)ylene, thiazol-(2,4- or 2,5-)ylene or imidazol-(1,4-, 2,4- or 2,5-)ylene, or a residue of their partially reduced or thoroughly reduced compounds, and the 6- membered heterocyclic group is, for example, pyridin-(2,4-, 2,5-, 2,6- or 3,5-)ylene, pyran-(2,4-, 2,5-, 2,6-, 2,5-, 2,6- or 4,6-)ylene, pyrazin-(2,5- or 2,6-)ylene, pyrimidin-(2,4- or 2,5-)ylene or pyridazin-3,5-ylene, or a residue of their partially reduced or thoroughly reduced compounds, among which thiophen-2,5-ylene, thiazol-2,5-ylene, pyridin-2,5-ylene, etc. are more suitable.

The lower alkylene group may be ethylene, trimethylene or tetramethylene.

The divalent heterocyclic group and lower alkylene group shown by —Ⓑ— may have 1 or 2 substituents such as a halogen (e.g. chlorine, bromine, fluorine or iodine), methoxy, dimethylamino, methyl, trifluoromethyl, or the like.

The process for preparing compounds (I) of this invention and their salts is explained in the following.

The compound (I) or its salt can be prepared by acylating a glutamic acid derivative of the formula (III) or its salt with a carboxylic acid (II) or its salt or reactive derivative at the carboxy group.

The acylation is carried out, for example, by reacting a compound (III) with a compound (II) or its reactive derivative in the presence of a carbodiimide, diphenylphosphorylazide or diethyl phosphorocyanidate. The amount of the compound (III) to be used is generally about 1–20 molar equivalents to the compound (II) or its reactive derivative, and preferably about 1–5 molar equivalents. The carbodiimide may be used usually in an amount of about 1–25 molar equivalents, preferably about 1–5 molar equivalents to the compound A practically suitable carbodiimide is dicyclohexylcarbodiimide, and the other carbodiimides such as diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-diethylaminopropyl)carbodiimide may also be used. The acylation is preferably carried out in a proper solvent such as water, alcohols (e.g., methanol, ethanol), ethers (e.g., dimethyl ether, diethyl ether, tetrahydrofuran, dioxane, monoglyme, diglyme), nitriles (e.g., acetonitrile), esters (e.g. ethyl acetate), halogenated hydrocarbons (e.g., dichloromethane, chloroform, carbon tetrachloride), aromatic hydrocarbons (e.g. benzene, toluene, xylene), acetone, nitromethane, pyridine, dimethyl sulfoxide, dimethylformamide, hexamethylphosphoramide, sulfolane or a proper mixture thereof. This reaction is usually carried out at a pH in the range of about pH 2 to 14, preferably about pH 6 to 9, at a reaction temperature from about −10° C. to boiling point of the solvent to be employed (about 100° C.), preferably about 0° to 50° C. in a reaction time of about 1 to 100 hours. The pH value of the reaction mixture may be optionally controlled with, for example, an acid (e.g., hydrochloric acid, sulfuric acid, phosphoric acid, nitric acid or acetic acid), a base (e.g., sodium methylate, sodium ethylate, sodium hydroxide, potassium hydroxide, barium hydroxide, lithium hydroxide, sodium carbonate, potassium carbonate, barium carbonate, calcium carbonate, sodium bicarbonate, trimethylamine, triethylamine, triethanolamine or pyridine) or a buffer (e.g., phosphate buffer, borate buffer or acetate buffer), if necessary. The reaction can be favorably carried out by using a catalyst which accelerates the acylation. The catalyst may be, for example, basic catalysts or acidic catalysts. The basic catalysts may be tertiary amines (e.g., an aliphatic tertiary amine such as triethylamine; an aromatic tertiary amine such as pyridine, α-, β- or γ-picoline, 2,6-lutidine, 4-dimethylaminopyridine, 4-(1-pyrrolidinyl)pyridine, dimethylaniline or diethylaniline), or the like, and the acidic catalysts may be Lewis acids [e.g., anhydrous zinc chloride, anhydrous aluminum chloride (AlCl$_3$), anhydrous ferric chloride, titanium tetrachloride (TiCl$_4$), tin tetrachloride (SnCl$_4$), antimony pentachloride, cobalt chloride, cupric chloride, boron trifluoride etherate, etc.], or the like. Among the above catalysts, 4-dimethylaminopyridine and 4-(1-pyrrolidinyl)pyridine are ordinarily preferable. The catalyst is used in an amount sufficient to accelerate the acylation, namely, in an amount of about 0.01–10 molar equivalents, preferably about 0.1–1 molar equivalent to the compound (II) or its reactive derivative. The reactive derivatives at the carboxy group of the carboxylic acid (II) may be, for example, the acid halides (e.g., fluoride, chloride, bromide or iodide), mixed acid anhydrides with other acids (e.g., iodoacetic anhydride or isobutyric anhydride), mixed acid anhydrides with lower monoalkyl carbonates (e.g., mono-methyl carbonate, mono-ethyl carbonate, mono-propyl carbonate, mono-iso-propyl carbonate, mono-butyl carbonate, mono-sec-butyl carbonate or mono-tert-butyl carbonate), active esters (e.g., cyanomethyl ester, carboethoxymethyl ester, methoxymethyl ester, phenyl ester, o-nitrophenyl ester, p-nitrophenyl ester, p-carbomethoxyphenyl ester, p-cyanophenyl ester or thiophenyl ester), acid azide, mixed acid anhydrides with phosphoric diesters (e.g., dimethyl phosphate, diethyl phosphate, dibenzylphosphate or diphenyl phosphate), mixed acid anhydride with phosphorous diesters (e.g., dimethyl phosphite, diethyl phosphite, dibenzyl phosphite or diphenyl phosphite), or the like.

Among the compounds (I) or salts thereof, a compound (I-1) or its salt where —COOR$^1$ and —COOR$^2$ are carboxy groups is preferably prepared by reacting a compound (III) where —COOR$^1$ and —COOR$^2$ are esterified carboxy groups, with a compound (II) or its reactive derivative at the carboxy group, and then deesterifying the resultant product by a conventional cleavage reaction or catalytic reduction. The cleavage reaction is, for example, a hydrolysis under basic condition (Method A), a hydrolysis under acidic condition (Method B-1), a cleavage reaction under acidic and nonaqueous condition (Method B-2), or the like. The base used in Method A is, for example, metallic alkoxides such as sodium methoxide, sodium ethoxide, sodium butoxide and potassium butoxide, metallic hydroxides such as sodium hydroxide., potassium hydroxide, lithium hydroxide and barium hydroxide, ammonia, amines such as triethylamine and pyridine, or the like. The acid to be used in Method B-1 is, for example, mineral acids such as hydrochloric acid and hydrobromic acid, sulfuric acid, nitric acid and phosphoric acid, organic acids such as trifluoroacetic acid, trichloroacetic acid, methanesulfonic acid, benzenesulfonic acid, p-toluenesulfonic acid and camphorsulfonic acid, or the like. The catalyst used in Method B-2 is, for example, mineral acids such as hydrogen chloride, hydrogen bromide, perchloric acid, sulfuric acid, nitric acid and phosphoric acid, organic acids such as trifluoroacetic acid, trichloroacetic acid, methanesulfonic acid, benzenesulfonic acid, p-toluenesulfonic acid and camphorsulfonic acid, Lewis acids such as anhydrous zinc chloride, anhydrous aluminum chloride (AlCl$_3$), anhydrous ferric chloride, titanium tetrachloride (TiCl$_4$), tin tetrachloride (SnCl$_4$), antimony pentachloride, cobalt chloride, cupric chloride and boron trifluoride etherate, or the like. The cleavage reaction is carried out in a proper solvent, at a temperature from 0° C. to the boiling point of the solvent employed, preferably at 10°–80° C., for 30 minutes to 2 days in each of the methods. The reaction solvent used in Method A and Method B-1 is, for example, water, methanol, ethanol, propanol, butanol, ethylene glycol, methoxyethanol, ethoxyethanol, tetrahydrofuran, dioxane, monoglyme, diglyme, pyridine, dimethylformamide, dimethyl sulfoxide or sulfolane, or a proper mixture thereof. In Method B-2, for example, ethyl acetate, dimethyl ether, diethyl ether, tetrahydrofuran, dioxane, monoglyme, diglyme, dichloromethane, chloroform, carbon tetrachloride, acetonitrile, benzene, toluene, xylene, nitromethane, pyridine or a proper mixture thereof is used as the reaction solvent. The catalytic reduction (Method C) is carried out in a proper solvent, at a temperature from about −40° C. to the boiling point of the solvent, preferably at about 0°–50° C. The solvent to be used is, for example, water, alcohols (e.g., methanol, ethanol, propanol, iso-propyl alcohol, butyl alcohol, sec-butyl alcohol, tert-butyl alcohol, ethylene glycol, methoxyethanol or ethoxyethanol), acetic acid esters (e.g., methyl acetate or ethyl acetate), ethers (e.g., dimethyl ether, diethyl ether, tetrahydrofuran, deoxane, monoglyme or diglyme), aromatic hydrocarbons (e.g., benzene, toluene or xylene), pyridine, dimethylformamide, or a proper mixture thereof. The catalyst used in the catalytic reduction is, for example, palladium, platinum, rhodium, Raney nickel, or the like. The reaction is preferably carried out by occasionally adding a small amount of acetic acid, trifluoroacetic acid, hydrochloric acid, sulfuric acid or the like.

The method for preparing a compound (I-1) is selected according to the nature of the groups —COOR$^1$ and —COOR$^2$. In general, Method A or Method B-1 is advantageously applied when —COOR$^1$ and —COOR$^2$ are carboxy groups esterified by methyl, ethyl, propyl, butyl, sec-butyl, phenyl or a substituted phenyl group, and Method B-2 is advantageously applied when —COOR$^1$ and —COOR$^2$ are carboxy groups esterified by iso-propyl or tert-butyl group, and Method B-1 or Method C is advantageously applied when —COOR$^1$ and —COOR$^2$ are carboxy groups esterified by a benzyl or a substituted benzyl group. In case where —COOR$^1$ and —COOR$^2$ are different from each other, the above Method A, Method B-1, Method B-2 and Method C are applied in an optional combination thereof.

The method for preparing the starting compounds (II) is explained in the following.

The compound (II) can be prepared by the following reaction steps.

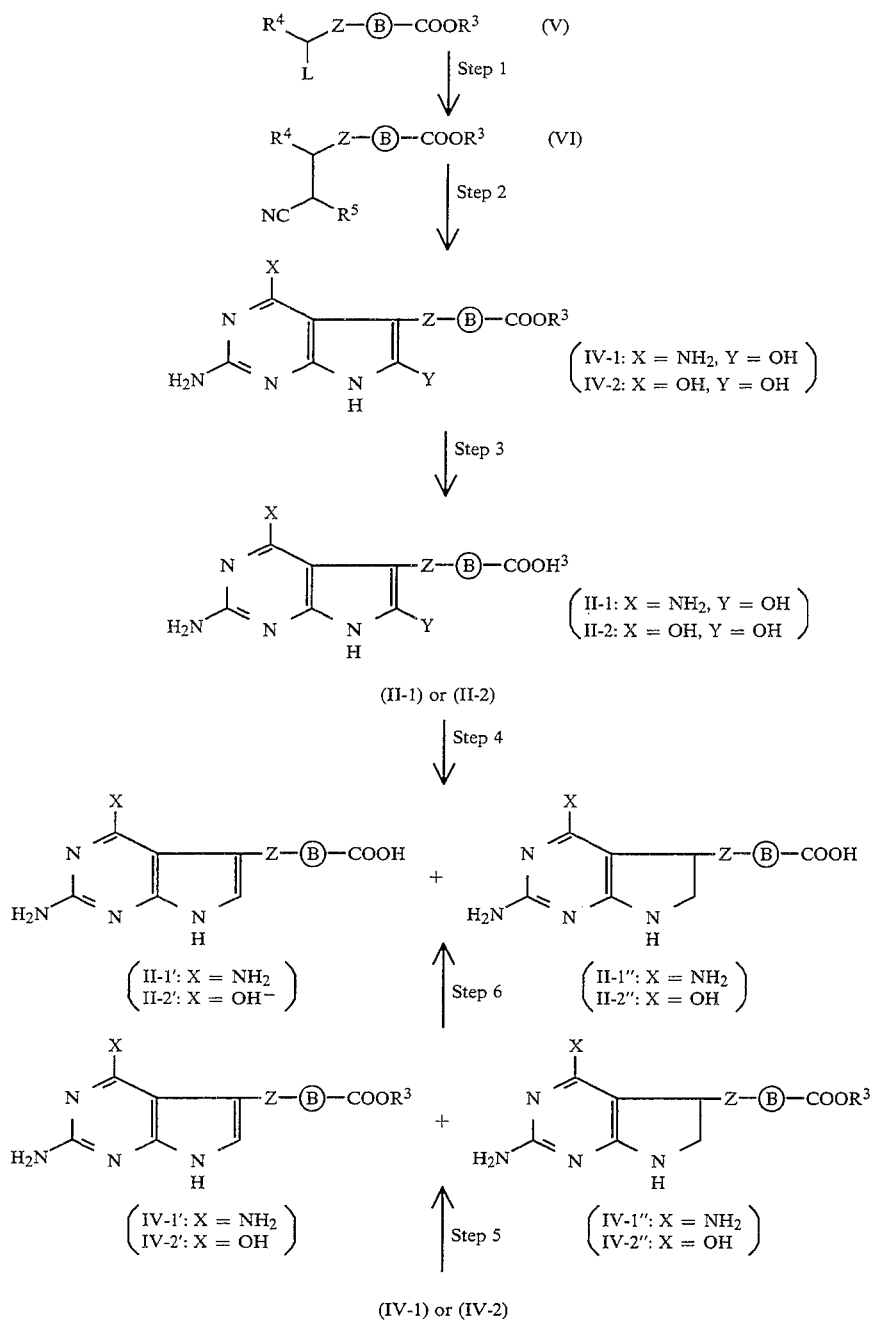

In the above steps, each of X, Y, $R^3$, —Ⓑ— ring and Z has the same meaning as above, respectively, and $R^4$ is an esterified carboxy group of the formula:—$COOR^6$, $R^5$ is a cyano group or an esterified carboxy group of the formula:—$COOR^6$, L is a halogen atom (e.g., chlorine, bromine or iodine) or a removable group easily derived from hydroxyl group (e.g., methanesulfonyloxy, benzenesulfonyloxy, p-toluenesulfonyloxy or trifluoromethanesulfonyloxy). The group $R^6$ in the esterified carboxy group of the formula:—$COOR^6$ is, for example, a $C_{1-4}$ lower alkyl (e.g., methyl, ethyl, propyl, iso-propyl, butyl, sec-butyl, tert-butyl, etc.), benzyl, a substituted benzyl (e.g., p-nitrobenzyl, p-methoxybenzyl, etc.), or the like.

The above reaction steps are explained in detail in the following.

Step 1

The starting compound (V) is subjected to the condensation reaction with malononitrile or a cyanoacetic acid ester [$NC\text{-}CH_2COOR^6$; $R^6$ has the same meaning as above] under a basic condition, to give the compound (VI). The bases, solvents and reaction conditions may be conventional ones.

Step 2

The compound (VI) is treated with guanidine, where it reacts the cyano group or ester group, followed by ring closure to form a pyrrolo[2,3-d]pyrimidine ring. The ring closure is carried out advantageously under a basic condition. The base used in this reaction is, for example, a metallic alkoxide such as sodium methoxide, sodium ethoxide and potassium tert-butoxide. The reaction solvent is, for example, methanol, ethanol, propanol, tert-butyl alcohol, dimethylsulfoxide, hexamethylphosphoramide, or the like. The reaction temperature is 0°–150° C., preferably 20°–100° C., and the reaction time is 1–48 hours.

Step 3

The compound (IV-1:X=$NH_2$, Y=OH, or IV-2:X=OH, Y=OH) obtained by the above Step 2 can be converted to the compound (II-1:X=$NH_2$, Y=OH, or II-2:X=OH, Y=OH) by subjecting the ester residue to the deesterification as used for the preparation of the compound (I-1).

Step 4

The compound (II-1 or II-2) obtained in the above Step 3 is subjected to a reduction to give a compound (II-1' and II-1":X=$NH_2$, Y=H, or II-2':X=OH, Y=H). The reduction can be carried out in a conventional manner, and for instance, reduction using metallic hydride (e.g., borane or alane, or ate complex thereof) is advantageously applied.

The Step 3 and Step 4 may be carried out in a reverse order. That is, a compound (IV-2 or IV-2) is reduced in a similar manner to the Step 4 to give a compound (IV-1' and IV-1":X=$NH_2$, Y=H, or IV-2' and IV-2":X=OH, Y=H) in the Step 5, and the resultant product is subjected to the deesterification reaction in a similar manner to the Step 3 to give a compound (II-1' and II-1", or II-2' and II-2") in the Step 6. The order of the deesterification and reduction may be selected in accordance with the nature of the substituent in the compound (IV-1 or IV-2).

The compounds (II) and (IV), where Y is hydrogen can be prepared by the following reaction steps, too.

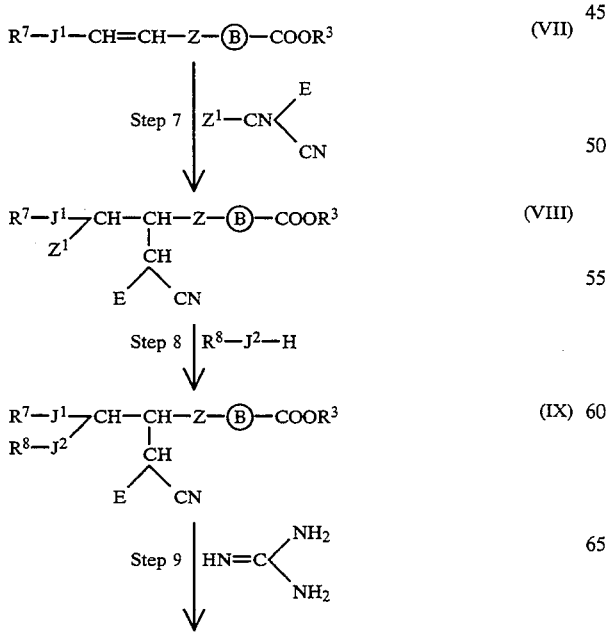

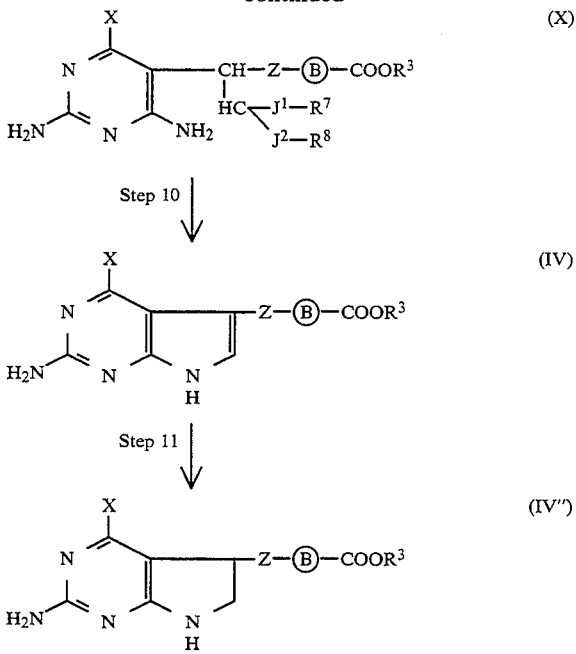

In the above steps, each X, $R^3$, —(B)— ring and Z has the same meaning as above, respectively, and $J^1$ and $J^2$ may be the same or different and each be an oxygen or sulfur atom, $R^7$ and $R^8$ may be the same or different and are each a hydrocarbon residue which may be substituted, $Z^1$ is a halogen atom (e.g., chlorine, bromine or iodine), and E is a cyano group or a group of the formula —$COOR^9$, —$CSOR^9$ or —$CSSR^9$. The hydrocarbon residues represented by $R^7$ and $R^8$ are, for example, a $C_{1-5}$ lower alkyl group (e.g., methyl, ethyl, propyl, iso-propyl, n-butyl, iso-butyl, sec-butyl, tert-butyl, n-pentyl, iso-pentyl, sec-pentyl, neo-pentyl or tert-pentyl), benzyl group, phenyl group, or the like. The lower alkyl group, benzyl group and phenyl group may have 1 to 3 substituents such as a halogen atom (e.g., fluorine, chlorine, bromine or iodine), nitro group, cyano group, an alkoxy group having 1 to about 4 carbon atoms (e.g., methoxy, ethoxy, propoxy, iso-propoxy, n-butoxy, iso-butoxy, sec-butoxy or tert-butoxy), a $C_{1-4}$ alkyl group (e.g., methyl, ethyl, propyl, iso-propyl, butyl, iso-butyl, sec-butyl or tert-butyl), an alkanoyl group having 1 to about 4 carbon atoms (e.g., formyl, acetyl, propionyl, n-butyryl or iso-butyryl), trifluoromethyl group, or the like.

The group $R^9$ in the formula —$COOR^9$, —$CSOR^9$ or —$CSSR^9$ is the hydrocarbon residues as exemplified for $R^7$ and $R^8$.

The above reaction steps are explained in detail in the following.

Step 7

The compound (VIII) can be prepared by addition of

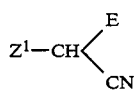

to the double bond ($R^7$—$J^1$—CH=CH—) in the compound (VII). The amount of the compound

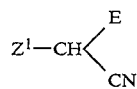

to be used is generally about 0.5–4 molar equivalents, preferably about 0.8–1.5 molar equivalents to the compound (VII). The reaction can be carried out in the presence of a proper solvent, at a temperature from about −10° C. to the boiling point of the solvent (about 100° C.), preferably at about 0° to 5° C., for about 30 minutes to 48 hours. The solvent used in the reaction is, for example, alcohols (e.g., methanol or ethanol), ethers (e.g., dimethyl ether, diethyl ether, tetrahydrofuran, dioxane, monoglyme or diglyme), nitriles (e.g., acetonitrile), esters (e.g., ethyl acetate), halogenated hydrocarbons (e.g., dichloromethane, chloroform or carbontetrachloride), aromatic hydrocarbons (e.g., benzene, toluene or xylene), or a proper mixture thereof.

The reaction can be advantageously carried out by radiating a light or by adding an organic peroxide. The organic peroxide is, for example, t-butyl hypochloride, peracetic acid, perbenzoic acid, p-chloro-perbenzoic acid, or the like. Thus obtained compound (VIII) is relatively reactive and can be used in the following step without isolation, though it can be isolated by a conventional method.

Step 8

The compound (VIII) obtained in Step 7 can be converted to the compound (IX) by reacting with an alcohol or thiol of the formula:$R^8$—$J^2$—H in the presence of an optional solvent, at a temperature from about −10° C. to the boiling point of the solvent employed (about 100° C.), preferably at about 0° to 50° C., for about 10 minutes to 24 hours. The solvent used in this reaction is, for example, ethers (e.g., dimethyl ether, diethyl ether, tetrahydrofuran, dioxane, monoglyme or diglyme), nitriles (e.g., acetonitrile), esters (e.g., ethyl acetate), halogenated hydrocarbons (e.g., dichloromethane, chloroform or carbon tetrachloride), aromatic hydrocarbons (e.g., benzene, toluene or xylene), or a proper mixture thereof. An excess amount of the alcohol or thiol of the formula:$R^8$-$J^2$-H can be used as the solvent, too.

Step 9

The compound (IX) is treated with guanidine in a proper solvent where it reacts with the cyano group, ester residue or thioester residue, to form a pyrimidine ring through cyclization and finally to give the compound (X). The reaction temperature is 0°–150° C., preferably 20°–100° C., and the reaction time is about 1–48 hours. .The reaction can be advantageously carried out under a basic condition. The bases to be used are, for example, metallic alkoxides such as sodium methoxide, sodium ethoxide and potassium tert-butoxide. The reaction solvents may be methanol, ethanol, propanol, tert-butyl alcohol, dimethyl sulfoxide or hexamethyl phosphoramide, or a proper mixture thereof.

Step 10

The group of the formula:

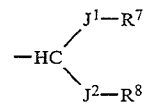

compound (X) is restored to a carbonyl group (—HC=O) which is followed by spontaneous intramolecular cyclization to give the compound (IV). The restoring reaction to a carbonyl group can be carried out by subjecting the compound (X) to a cleavage reaction, which can be carried out without any solvent or in a proper solvent, at a reaction temperature of about −10° C. to the boiling point of the solvent (about 100° C.), preferably about 0°–50° C., for about 10 minutes to 100 hours. The cleavage reaction may be, for example, the hydrolysis under acidic condition (Method B-1), the cleavage reaction under acidic and nonaqueous condition (Method B-2), the catalytic reduction (Method C), the cleavage reaction using a metal salt (Method D), the cleavage reaction using an oxidizing agent (Method E), or the like. The Methods B-1, B-2 and C can be carried out in the same way as the cleavage reaction of the groups of —$COOR^1$ and —$COOR^2$ as explained before. The metal salt used in Method D is, for example, cupric chloride, silver nitrate, silver oxide, mercuric chloride, tellurium salt (e.g., tellurium nitrate or tellurium trifluoroacetate), or the like. The oxidizing agent to be used in Method E is, for example, oxygen-light, hydrogen peroxide, perbenzoic acid, m-chloro-perbenzoic acid, perchlorates (e.g., lithium perchlorate, silver perchlorate, mercuric perchlorate or tetrabutylammonium perchlorate), nitrosyl sulfuric acid, alkyl nitrites (e.g., isoamyl nitrite), iodine, bromine, chlorine, N-bromosuccinimide, sulfuryl chloride, chloramine-T, or the like. The method for restoring to the carbonyl group (>C=O) is selected in accordance with the chemical nature of groups of —$J^1$—$R^7$ and —$J^2$—$R^8$. The reaction solvent used in Methods D and E is, for example, water, alcohols (e.g., methanol, ethanol, propanol, isoporpyl alcohol, butyl alcohol, sec-butyl alcohol, tert-butyl alcohol, ethylene glycol or methoxyethanol), ethers (e.g., dimethyl ether, diethyl ether, tetrahydrofuran, dioxane, monoglyme or diglyme), aromatic hydrocarbons (e.g., benzene, toluene or xylene), halogenated hydrocarbons (e.g., dichloromethane, chloroform or carbon tetrachloride), acetone, acetonitrile, or a proper mixture thereof.

The intramolecular cyclization reaction in the step for preparing the compound (IV) is usually carried out in the course of the restoration to the carbonyl group (>C=O) or after the restoration by spontaneous condensation of the amino group or the pyrimidine ring to form pyrrolo[2,3-d]pyrimidine ring. The cyclization can be carried out in a short time and in a high yield in the presence of an acidic catalyst. The acidic catalysts may be the mineral acids, organic acids or Lewis acids as exemplified in the above Methods B-1 and B-2.

Step 11

The compound (IV) where the ring A is a pyrrole ring obtained in the above Step 10 can be easily converted, if necessary, to the compound (IV'') where the ring A is a pyrroline ring by a catalytic reduction. The above mentioned Method C can be advantageously applied to this catalytic reduction.

Further, the compound (IV) or compound (IV'') can be converted, if necessary, to the compound (II) or compound (II'') by subjecting it to a deesterification reaction in a similar manner to the aforementioned Step 3.

The reactions, reagents, reaction conditions or protecting groups optionally applied to each functional group in the above Step 1 to Step 11 and the steps for preparing the starting compounds (III), (V) and (VII) are known and explained in detail in the following literature. J. F. W. McOmine, Protective Groups in Organic Chemistry, Plenus Press, London and New York (1973); Pyne Hendrickson Hamond, Organic Chemistry, 4th Edition [I]–[II], Hirokawa Shoten (1982); and M. Fieser and L. Fieser, Reagents for Organic Synthesis Vol. 1–13, Wiley-Interscience, New York, London, Sydney and Toronto (1968–1988).

Further, the amino group, hydroxy group or mercapto group represented by X in the compounds (I), (II) and (IV) can be converted to each other, if necessary, in accordance with a conventional conversion reaction of substituents on a pyrimidine ring [see Peptide, Nucleic Acid and Enzyme, Extra issue, Chemical Synthesis of Nucleic acid, Kyoritsu Shuppan (1968)].

The compounds (I), (II) and (IV) of this invention prepared by these steps and the starting compounds and products in each step can be isolated from the reaction mixture by a conventional means for isolation and purification, for example, concentration, extraction with solvent, chromatography, recrystallization, or the like.

The compounds (I) obtained by the preparation method of this invention and the starting compounds (II) and (IV) may be in the salt form. The salts with base may be the salts with alkali metal, alkali earth metal, non-toxic metal, ammonium and substituted ammonium, for example, sodium, potassium, lithium, calcium, magnesium, aluminum, zinc, ammonium, trimethylammonium, triethylammonium, triethanolammonium, pyridinium, substituted pyridinium salt or the like. The salts with acid may be the ones with mineral acids such as hydrochloric acid, sulfuric acid, nitric acid, phosphoric acid and boric acid, or with organic acids such as oxalic acid, tartaric acid, acetic acid, trifluoroacetic acid, methanesulfonic acid, benzenesulfonic acid, p-toluensulfonic acid and camphorsulfonic acid.

ACTIVITY

The compounds (I) of this invention or their salts show an excellent antitumor effect against mouse tumor cell strains (P388, L1210, L5178Y, B16 melanoma, Meth A, Lewis Lung Carcinoma, S180 sarcoma, Ehrlich Carcinoma, Colon 26 and 38, etc.) and human tumor cell strains (HL60, KB, etc.), an activity to decrease the tumors possessed by warm-blooded animals (e.g., leukemia, melanoma, sarcoma, mastocytoma, carcinoma, neoplasia, etc.) and an activity to prolong the life-span of warm-blooded animals suffering from tumors.

The test results indicating pharmacological activity of the compounds (I) of this invention or their salts are described in the following.

The cell growth inhibiting effect ($IC_{50}$) on KB cells of the compounds obtained in the following Examples was measured by the following method. (Hereinafter, % means weight %.)

Human epidermoid carcinoma KB cells ($1 \times 10^4$/ml) prepared by a conventional method were inoculated in a volume of 0.1 ml for each hole of the 96-microwell plate, and cultured at 37° C. for 24 hours without agitation in an atmosphere of 5% $CO_2$. A 10% solution of one compound obtained by Example in 10% MEM (minimal essential medium, Nissui Pharmaceutical Co. Ltd, Japan) was added thereto, and the cells were cultured again at 37° C. for 72 hours without agitation in an atmosphere of 5% $CO_2$. The culture was removed by using a micropipet, and another 10% solution 0.1 ml of MTT [3-(4,5-dimethylthiazol-2-yl)-2,5-diphenyltetrazolium bromide] (Dojin Laboratories, Japan) in 10% MEM (1.0 mg/ml) was added thereto. The cells were cultured at 37° C. for 4 hours. A 10% SDS [sodium dodecylsulfate](Wako Pure Chimicals, Japan) solution (0.1 ml) was further added, and the cells were cultured at 37° C. for 24 hours. The absorbance at 590 nm was measured, and the concentration of a drug needed for decreasing the number of cells in non-treated control group to a degree of 50% was determined as $IC_{50}$ value of the compound. The result is shown in Table 1.

TABLE 1

| Sample compound | $IC_{50}$ (µg/ml) |
|---|---|
| Compound of Example 3 | 0.00043 |

As shown in the above test result, the compound (I) or its salt are excellent in inhibition of growth of KB cells of human epidermoid carcinoma. Further, the compound (I) of this invention or its salt is of low toxicity to a living body and has a remarkable antitumor activity.

Accordingly, a pharmacentical composition containing the compound (I) or its salt can be used as an antitumor agent for treating tumors in warm-blooded animals, especially mammals (e.g. mouse, rat, cat, dog or rabbit).

The compound (I) or its salt can be administered orally or parenterally as an antitumor agent by itself or in a conventional form of, for example, powders, granules, tablets, capsules, suppositories or injections, which can be prepared by using a pharmacentically acceptable carrier, excipient or diluent, etc.

The dosage varies depending on subject animals, diseases, conditions kind of compounds, administration routes, etc. In case of oral administration, the dosage of the compound (I) of this invention or its salt is about 2.0–200 mg/kg body weight, preferably 5.0–100 mg/kg body weight per day for warm-blooded animals, and in case of parenteral administration, it is about 1.0–100 mg/kg body weight, preferably 3.0–50 mg/kg body weight per day for warm-blooded animals. The administration route as an injection is intramuscular, abdominal, subcutaneous or intravenous injection, etc.

The above-mentioned preparations can be formulated by a conventional method. The preparations for oral administration, for example, tablets can be prepared by optionally mixing a binding agent (e.g., hydroxypropylcellulose, hydroxypropylmethylcellulose, macrogol, etc.), a disintegrating agent (e.g., starch, carboxymethycellulose calcium, etc.), a lubricant (e.g., magnesium stearate, talc, etc.), and the like.

And, the preparation for parenteral administration, for example, injection can be prepared by optionally adding an agent to provide isotonicity (e.g., glucose, D-sorbitol, D-mannitol, sodium chloride, etc.), a preservative (e.g., benzyl alcohol, chlorobutanol, methyl p-hydroxybenzoate, propyl p-hydroxybenzoate, etc.), a buffer (e.g., phosphate buffer, sodium acetate buffer, etc.), and the like.

As a method for preparing e.g., tablets, a compound (I) of this invention or its salt (about 1.0–25 mg), lactose (100–500 mg), corn starch (about 50–100 mg) and hydroxypropylcellulose (about 5–20 mg) for each tablet are mixed and granulated in a conventional manner, and corn starch and magnesium stearate are mixed with the granules, and the mixture is compressed to give tablets of about 100–500 mg/tablet with a diameter of about 3–10 mm. Thus prepared tablets are coated with an about 5–10% solution of hydroxypropylmethylcellulose phthalate (about 10–20 mg) and castor oil (about 0.5–2 mg) in a mixture of acetone and ethanol for each tablet to give enteric-coated tablets.

An injection can be prepared, for example, by dissolving a sodium salt (about 2.0–5.0 mg) of a compound (I) of this invention in physiological saline (about 2 ml) for each ampoule, filling the solution in each ampoule, sealing and sterilizing at about 110° C. for about 30 minutes, or by dissolving a sodium salt (about 2.0–5.0 mg) of a compound (I) in distilled and sterilized water (about 2 ml) containing mannitol or sorbitol (about 10–40 mg) for each ampoule, filling the solution in each ampoule, lyophilizing and then sealing. The injection prepared by lyophilization can be administered subcutaneously, intravenously or intramuscularly after dissolving it in physiological saline in a concentration of about 1.0–25 mg/ml of the sodium salt of a compound (I).

This invention is explained in the following with Reference Examples.

REFERENCE EXAMPLE 1

Preparation of tert-butyl 5-formyl-2-thiophenecarboxylate

5-Formyl-2-thiophenecarboxylic acid (12.3 g) and tert-butyl alcohol (58.38 g) were dissolved in dichloromethane (150 ml). To the solution were added a solution of dicyclohexylcarbodiimide (19.49 g) in dichloromethane (50 ml) and a solution of 4-dimethylaminopyridine (0.96 g) in dichloromethane (10 ml), and the mixture was stirred at room temperature for 16 hours. The precipitates were removed by filtration, and the filtrate was concentrated. The resultant residue was purified by silica gel column chromatography (developing solvent: ethyl acetate-hexane=1:99→5:95) to give the captioned compound (11.76 g).

IR (KBr): 2990, 2810, 1710, 1680, 1365, 1290, 1220, 1160, 1030 cm$^{-1}$.

$^1$H-NMR (CDCl$_3$) δ: 1.59(9H,s), 7-71(1H,d,J=4 Hz), 7.76 (1H,d,J=4 Hz ), 9.96(1H,s).

REFERENCE EXAMPLE 2

Preparation of tert-butyl 5-(4-hydroxy-1-butenyl)2-thiophenecarboxylate

In an atmosphere of argon gas, (3-hydroxypropyl)triphenylphosphonium bromide (10.04 g) was added to a suspension of sodium hydride (0.6 g) in tetrahydrofuran (60 ml), and the mixture was refluxed under heating for 4 hours. To the mixture was added a solution of the compound (5.31 g) obtained in the above Reference Example 1 in tetrahydrofuran (20 ml), and the mixture was refluxed under heating for 2 hours. The solvent was distilled off under reduced pressure, and ether (150 ml ) was added to the residue. The insoluble substance was filtered off in the presence of celite. The filtrate was concentrated under reduced pressure and the residue was purified by silica gel column chromatography (developing solvent: hexane-ethyl acetate=10: 1→4:1 ) to give the captioned compound (5.46 g).

IR (Neat): 3400, 2980, 1700, 1520, 1440, 1365, 1290, 1245, 1160, 1090, 1040cm$^{-1}$.

$^1$H-NMR (CDCl$_3$) δ: 1.57(9H,s), 2.47(0.8H,q,J=6.2 Hz), 3.72-3.88(2H,m), 5.77(0.6H,dt,J=11.44 Hz,7.6 Hz), 6.20(0.4H,dt,J=14 Hz,7.6 Hz), 6,58(0.4H, d,J=15.8 Hz), 6.33(0.6H,d,J=11.6 Hz), 6.86(0.4H,d,J=3.6Hz), 7.61(0.6H,d,J=3.6 Hz).

REFERENCE EXAMPLE 3

Preparation of tert-butyl 5-(4-hydroxybutyl)-2-thiophenecarboxylate

The compound (5.46 g) obtained in the above Reference Example 2 was dissolved in ethanol (100 ml). To the solution was added 10% palladium-carbon (5.46 g), and the mixture was stirred in an atmosphere of hydrogen gas for 1 hour. The catalyst was filtered off by using celite, and the filtrate was concentrated under reduced pressure to give the captioned compound (5.25 g).

IR (Neat): 3400, 2940, 1710, 1540, 1460, 1370, 1295, 1165, 1095 cm$^{-1}$.

$^1$H-NMR (CDCl$_3$) δ: 1.56(9H,s), 1.59-1.66 (2H,m), 1.70-1.85(2H,m), 2.86(2H,t, J=7.4 Hz), 3.67(2H,t,J=6 Hz), 6.76(1H, d,J=3.6 Hz), 7.54(1H,d,J=3.6 Hz).

REFERENCE EXAMPLE 4

Preparation of tert-butyl 5-(4-oxobutyl)-2-thiophenecarboxylate

A solution of dimethyl sulfoxide (3.81 g) in dichloromethane (10 ml) was added to a solution of oxalyl chloride (3.09 g) in dichloromethane (30.9 ml) at −60° C., and the mixture was stirred for 2 minutes. To the mixture was added a solution of the compound (5.2 g) obtained in the above Reference Example 3 in dichloromethane (20 ml) at the same temperature, and the mixture was stirred for 15 minutes. Triethylamine (10.27 g) was added dropwise to the mixture and stirred for 5 minutes. After raising the reaction temperature to 0° C. in 30 minutes, the reaction mixture was poured into water (250 ml) and extracted with dichloromethane. The extract was concentrated under reduced pressure, and the residue was purified by silica gel column chromatography (developing solvent: ethyl acetate-hexane=3:97→5:95) to give the captioned compound (4.19 g).

IR (Neat): 2980, 2940, 1730, 1700, 1460, 1370, 1300, 1280, 1170, 1100 cm$^{-1}$.

$^1$H-NMR (CDCl$_3$) δ: 1,57(9H,s), 2.02(2H,q, J=7.2 Hz), 2.52(2H,t,J=7.2 Hz), 2.87(2 H,t,J=7.2 Hz), 6.76(1H,d,J=3.6 Hz), 7.55 (1H,d,J=3.6 Hz).

REFERENCE EXAMPLE 5

Preparation of tert-butyl 5-(5-methoxy-4-pentenyl)-2-thiophenecarboxylate

A solution of potassium tert butoxide(1 mole) in tetrahydrofuran (21.8 ml) was added to a solution of (methoxymethyl)triphenylphosphonium chloride (7.48 g) in toluene (25 ml) at 0° C. and stirred for 10 minutes. To the mixture was added dropwise at the same temperature a solution of the compound (5.04 g) obtained in the above Reference Example 4 in toluene (25 ml), and the mixture was stirred at room temperature for 2 hours. Ether (150 ml) was added to the reaction mixture, and the organic layer was separated, washed with water and then with saturated saline and dried over anhydrous sodium sulfate. The solvent was distilled off under reduced pressure, and the resultant residue was purified by silica gel column chromatography (developing solvent: ethyl acetate-hexane=1:49) to give the captioned compound (4.71 g).

IR (Neat): 2970, 2930, 1705, 1650, 1455, 1360, 1295, 1250, 1165, 1090 cm$^{-1}$.

$^1$H-NMR (CDCl$_3$) δ: 1.56(9H,s), 1.73(2H,q, J=7.2 Hz), 1.94–2.18(2H,m), 2.81(2H,t, J=7.2 Hz), 3.51(1.8H,s), 3.59(1.2H,s), 4.33(0.4H,q,J=7.2 Hz), 4.70(0.6H,dt,J=7.2 Hz,12.8 Hz), 6.74(1H,d,J=3.8 Hz), 7.54(1H,d,J=3.8 Hz).

REFERENCE EXAMPLE 6

Preparation of tert-butyl 5-[5,5-dicyano-4-(dimethoxymethyl)pentyl]-2-thiophenecarboxylate In an atmosphere of argon gas, bromomalononitrile (2.555 g) and the compound (4.15 g) obtained in the above Reference Example 5 were dissolved in dichloromethane (82.5 ml). Molecular sieve 3A (2.1 g) was added to the mixture, and the mixture was irradiated with UV light by using a UV lamp for analysis without filter for 2.5 hours. To the reaction mixture was added methanol (5.11 ml), and the mixture was stirred for 15 minutes, poured into ice-water containing 2N potassium carbonate solution (18 ml) and extracted with dichloromethane. The extract was washed with water and dried over anhydrous sodium sulfate. The solvent was distilled off under reduced pressure, and the resultant residue was purified by silica gel column chromatography (developing solvent: ethyl acetate-hexane=1:19→1:9) to give the captioned compound (3.95 g).

IR (Neat): 2980, 2940, 2250, 1700, 1455, 1365, 1300, 1280, 1165, 1095 cm$^{-1}$.

$^1$H-NMR (CDCl$_3$) δ: 1.56(9H,s), 1.68–1.97 (4H,m), 2.21–2.33(1H,m), 2.89(2H,t,J=7 Hz), 3.42(3H,s), 3.46(3H,s), 4.12(1H, d,J=4 Hz), 4.33(1H,d,J=5.2 Hz), 6,79(1H, d,J=3.6 Hz), 7.55(1H,d,J=3.6 Hz).

REFERENCE EXAMPLE 7

Preparation of tert-butyl 5-[4-(2,4,6-triaminopyridine-5-yl)-5,5-dimethoxypentyl]-2-thiophenecarboxylate In an atmosphere of argon gas, guanidine hydrochloride (841 mg) was suspended in tert-butyl alcohol (14.5 ml). A solution of potassium tert-butoxide (1 mole) in tetrahydrofuran (8.8 ml) was added to the suspension and stirred for 10 minutes. To the mixture was added a solution of the compound (3.03 g) obtained in the above Reference Example 6 in tert-butyl alcohol (43.8 ml), and the mixture was refluxed under heating for 2 hours. The reaction mixture was poured into ice-water (150 ml) and extracted with dichloromethane. The extract was dried over anhydrous sodium sulfate, and the solvent was distilled off under reduced pressure. The resultant residue was purified by silica gel column chromatography (developing solvent: dichloromethanemethanol=30:1→19:1) to give the captioned compound (3.50 g).

IR (KBr): 3470, 3350, 2980, 2940, 1700, 1610, 1560, 1435, 1365, 1290, 1165, 1095 cm$^1$.

$^1$H-NMR (CDCl$_3$/CD$_3$OD) δ: 1,56(9H,s), 1.57−1.76(2H,m), 1.86–2.10(2H,m), 2,78(2H, t,J=6.6 Hz), 2.74–2.87(1H,m), 3.48(3H, s), 3.52(3H,s), 4.38(1H,d,J=3 Hz), 6.72 (1H,d,J=3.6 Hz), 7.53(1H,d,J=3.6 Hz)

REFERENCE EXAMPLE 8

Preparation of methyl 5-[5-(tert-butoxycarbonyl)thiophen-2-yl]pentanoate

In an atmosphere of argon gas, potassium (25 g) was added to dried tert-butanol (820 ml) and refluxed for 3 hrs to give a solution. To the solution cooled to 20° C. was added diethyl ether (300 ml) and then slowly added a solution of methyl crotonate (63.93 g) and tert-butyl 5-formyl-2-thiophenecarboxylate (73.1 g) in tert-butanol/diethyl ether (2:1, 300 ml) keeping an inner temperature to 10° C. The mixture was stirred for 2 hrs at the same temperature and adjusted to pH 4 by adding 1N-potassium hydrogen sulfate aqueous solution (750 ml) under cooling. The mixture was extracted with diethyl ether, and the extract was washed with water and then saturated saline solution and distilled under reduced pressure to remove the solvent. The residue was dissolved in ethyl acetate (100 ml), to which 5% Pd-C (15 g:commercially available from Engelhard) was added. The mixture was vigorously stirred for 3 hrs at room temperature under hydrogen pressure of 4 kg/cm$^2$. The reaction mixture was filtered to remove the catalyst and the filtrate was distilled under reduced pressure to remove the solvent. To the resulting residue were added dry methanol (200 ml), 4-(N,N-dimethylamino)pyridine (30 mg) and dichloromethane (250 ml), to which a solution of 1,3-dicyclohexylcarbodiimide (132 g) in dichloromethane (250 ml) was added slowly dropwise at 0° C. The mixture was stirred for 18 hrs at room temperature and cooled to 0° C. After adding acetic acid (30 ml), the mixture was stirred for 30 mins at 0° C. and for 30 mins at room temperature. The resulting precipitate was filtered off and the filtrate was concentrated to dryness under reduced pressure. Ethyl acetate (100 ml) was added to the residue and allowed to stand for 2 hrs at 0° C. Again, the resulting precipitate was filtered off and the filtrate was concentrated under reduced pressure. The residue was purified by silica gel column chromatography using diethyl ether-hexane=1:15→1:5, to obtain the captioned compound (61.4 g).

IR (Neat): 2980, 2950, 1740, 1712, 1540 cm$^{-1}$.

$^1$H-NMR (CDCl$_3$) δ: 1.56(9H,s), 1.60–1.81(4H,m), 2.37(2H,t,J=7 Hz), 2.87(2H,t, J=7 Hz), 3.67(3H,s), 6.77(1H, d,J=3.6 Hz), 7.55(1H,d,J=3.6 Hz).

REFERENCE EXAMPLE 9

Preparation of methyl 5-[5-(tert-butoxycarbonyl)thiophen-2-yl]-2-iodopentanoate

In an atmosphere of argon gas, a solution of n-butyl lithium (24.5 mmol) in hexane (15.3 ml) was added in to a solution of diisopropylamine (2.48 g) tetrahydrofuran (100 ml) and stirred for 10 mins. To this solution was dropwise added a solution of the compound of Reference Example 8 (6.66 g) in tetrahydrofuran (50 ml) at −78° C. taking 30 mins, followed by stirring for 30 mins. Then, a solution of iodine (5.66 g) in tetrahydrofuran (30 ml) was added to the above mixture and stirred for 20 mins. The reaction mixture was allowed to rise to 0° C. in 30 mins, adjusted to pH 4 by adding 1N-potassium hydrogen sulfate aqueous solution (30 ml) and extracted with diethyl ether. The extract as collected was washed with 1N-potassium carbonate aqueous solution and then saturated saline solution, dried over anhydrous magnesium sulfate and distilled under reduced pressure to remove the solvent. The residue was purified by silica gel column chromatography using diethyl ether:hexane=1:9 to obtain the captioned compound (4.90 g).

IR (Neat): 2990, 2905, 1744, 1718, 1536 cm$^{-1}$.

$^1$H-NMR (CDCl$_3$) δ: 1.55(9H,s), 1.61-2.10(4H, m), 2.88(2H,t,J=7 Hz), 3.87 (3H,s), 4.35(1H,t,J=7 Hz), 6.75(1H,d,J=3.6 Hz), 7.55(1H, d,J=3.6 Hz).

REFERENCE EXAMPLE 10

Preparation of methyl 5-[5-(tert-butoxycarbonyl) thiophen-2-yl]-2-(dicyanomethyl)pentanoate A solution of malononitrile (3.37 g) in dimethyl sulfoxide (8 ml) was added to a suspension of sodium hydride (1.356 g) in dimethyl sulfoxide (8 ml) under ice-cooling, to which a solution of the compound of Reference Example 9 (4.80 g) in dimethyl sulfoxide (12 ml) was dropwise added and stirred for an hour at room temperature. The mixture was adjusted to pH 4 by adding 1N-potassium hydrogen sulfate aqueous solution (45 ml) at 0° C. and extracted with diethyl ether. The ethereal layer was washed with water, dried over anhydrous magnesium sulfate and distilled under reduced pressure to remove the solvent. The residue was purified by silica gel column chromatography using ethyl acetate:hexane=1:5 to obtain the captioned compound (3.45 g).

IR (Neat): 2970, 2930, 2252, 1740, 1713, 1540 cm$^{-1}$.

$^1$H-NMR (CDCl$_3$) δ: 1.47(9H,s), 1.65-2.04(4H, m), 2.89(2H,t,J=7 Hz), 2.95-3.20(1H,m), 3.92 (3H,s), 4.02(1H,d,J=7 Hz), 6.75(1H,d,J=3.6 Hz), 7.57 (1H,d,J=3.6 Hz).

REFERENCE EXAMPLE 11

Preparation of methyl 8-methoxycarbonyl-2-iodooctanoate

The captioned compound (7.5 g) was obtained by treating dimethyl azelate (21.7 g) in the same way as in Reference Example 9.

$^1$H-NMR (CDCl$_3$) δ: 1.10-2.01(10H,br. ,m), 2.30(2H,t,J=7 Hz), 3.70 (3H,s), 3.86(3H,s), 4.33 (1H,t,J=7 Hz).

REFERENCE EXAMPLE 12

Preparation of methyl 8-methoxycarbonyl-2(dicyanomethyl)octanoate

The captioned compound (5.28 g) was obtained by treating the compound of Reference Example 11 (9.92 g) in the same way as in Reference Example 10.

$^1$H-NMR (CDCl$_3$) δ: 1.12-2.04(10H,br.m), 2.32(2H,t,J=7 Hz), 2.90-3.20(1H,m), 3.73 (3H,s), 3.92(3H,s), 4.07(1H,d,J=7 Hz).

REFERENCE EXAMPLE 13

Preparation of methyl 5-[3-(2-amino-7-benzyl-3-isopropyloxymethyl-4(3H)-oxopyrrolo[2,3-d]pyrimidin-5-yl)-1-oxopropen-2-yl]-2-thiophenecarboxylate 2-Amino-7-benzyl-3-isopropyloxymethyl-4(3H)-oxopyrrolo[2,3-d]pyrimidine-5-carbaldehyde (1.7 g) was suspended in a mixture of methanol and tetrahydrofuran (10:1, 33 ml) and then dissolved by adding a solution of sodium methylate in methanol (6.25 mM, 3.75 ml). To the resulting solution was added methyl 5-acetyl-2-thiophenecarboxylate (2.30 g), followed by stirring for 15 hrs at room temperature. The mixture was distilled under reduced pressure to remove the solvent, and the residue was purified by silica gel column chromatography using hexane containing 5~25% ethyl acetate to obtain the captioned compound (2.11 g).

IR (KBr): 3480, 3350, 1710, 1680, 1620, 1550, 1535, 1375, 1280, 1210, 1110, 1060, 775 cm$^{-1}$.

$^1$H-NMR (CDCl$_3$) δ: 1.25(6H,d,J=6 Hz), 3.90 (3H,s), 3.82-4.05(1H,m), 5.17(2H,S), 5.60(2H,s), 6.91(1H,s), 7.12-7.41 (5H,m), 7.65(2H,s), 7.71 (1H,d,J=15 Hz), 8.58(1H, d,J=15 Hz).

REFERENCE EXAMPLE 14

Preparation of methyl 5-[3-(2-amino-3-isopropyloxymethyl-4(3H)-oxo-5,6-dihydropyrrolo[2,3-d]pyrimidin-5-yl)propyl]-2-thiophenecarboxylate To a solution of the compound of Reference Example 13 (2.0 g) in methanol-tetrahydrofuran mixture (3:4, 350 ml) were added 1N-hydrochloric acid (8 ml) and 10% Pd-C (4 g, Engelhard's product). The catalytic hydrogenation was conducted for 48 hrs in hydrogen atmosphere. The reaction mixture was filtered to remove the catalyst, and the filtrate was neutralized and distilled under reduced pressure to remove the solvent. The residue was purified by silica gel column chromatography (developing solvent: chloroform containing 2-4 % ethanol ) to obtain the captioned compound (0.69 g).

IR (KBr): 3210, 2980, 1725, 1625, 1540, 1510, 1435, 1275, 1175, 1100, 1060 cm$^{-1}$.

$^1$H-NMR (CDCl$_3$) δ: 1.18(3H,d,J=6 Hz), 1.20 (3H,d,J=6 Hz), 1.51-2.15 (4H,m), 2.84(2H,t,J=7 Hz), 3.06-3.79(3H,m), 3.81-4.06 (1H,m), 3.89(3H,s), 5.04 & 5.58(2H,ABq,J=12 Hz), 6.85 (1H,d,J=3.6 Hz), 7.50(1H,d, J=3.6 Hz).

EXAMPLE 1

Preparation of 5-[3-(2,4-diamino-7H-pyrrolo[2,3-d]pyrimidine-5-yl)propyl]-2-thiophenecarboxylic acid The compound (1.32 g) obtained in the above Reference Example 7 was dissolved in mixture of trifluoroacetic acid (7 ml) and water (0.2 ml) and stirred at room temperature for 2 hours. The solvent was distilled off under reduced pressure and the residue was dried at 90° C. to give trifluoroacetic acid salt of the captioned compound quantitatively.

IR (KBr): 3440, 3120, 1700, 1690, 1650, 1455, 1290, 1195, 1150, 820, 800 cm$^{-1}$.

$^1$H-NMR (Me$_2$SO-d$_6$) δ: 1.18-1.96(2H,m), 2.75(2H,t,J=7.6 Hz), 2,89(2H,t,J=7-6 Hz), 6.76(1H,s), 6.94(H,d,J=3-8 Hz),7-15(2H, bs), 7.57(1H,d,J=3-8 Hz), 7.77(2H, bs), 11.52(1H,s).

EXAMPLE 2

Preparation of diethyl N-[5-(3-(2,4-diamino-7Hpyrrolo[2,3-d]pyrimidin-5-yl)propyl)-2-thenoyl]-L-glutamate The entire amount of the compound obtained in the above Example 1 and diethyl glutamate hydrochloride (1.08 g) were dissolved in dimethyl formamide (30 ml). To the solution were added dropwise at 0° C. a solution of diethyl phosphorocyanidate (0.514 g) in dimethyl formamide (4 ml) and triethylamine (1.37 g) in dimethyl formamide (4 ml) in turn. The mixture was stirred at the same temperature for 30 minutes and then at room temperature for 3 hours. The solvent was distilled off under reduced pressure and the resultant residue was purified by silica gel column chromatography (developing solvent: dichloromethane separated from conc. aqueous ammonia→ethanol containing 10% ammonia-dichloromethane=1:29→1:19) to give the captioned compound (1.11 g) as colorless crystals.

IR (KBr ): 3380, 2980, 1735, 1630, 1605, 1575, 1545, 1455, 1425, 1380, 1200, 1090, 1010 cm$^{-1}$.

$^1$H-NMR (CDCl$_3$/CD$_3$OD) δ: 1.23(3H,t,J=7.6 Hz), 1.30(3H,t,J=7.6 Hz), 2.01-2.38(4H, m),2.42-2.54(2H,m), 2.71(2H,t,J=7.2 Hz), 2.91(2H,t,J=7.2 Hz),4.11(2H,q,J=7.6 Hz), 4.23(2H,q,J=7.6 Hz), 4.66-4.76(1H,m), 6.50(1H,s), 6.70(1H,d,J=3.6 Hz), 7.43 (1H,d,J=3.6 Hz).

EXAMPLE 3

Preparation of N-[5-(3-(2,4-diamino-7H-pyrrolo[2,3-d]pyrimidin-5-yl)propyl)-2-thenoyl]-L-glutamic acid The compound (1.05 g) of Example 2 was dissolved in a mixed solvent of tetrahydrofuran and water (1:1, 30 ml). 1N-Aqueous solution of sodium hydroxide (6.27 ml) was added to the solution. The mixture was stirred at room temperature for 1.5 hours and concentrated under reduced pressure to a volume of 15 ml. The resultant insoluble substance was filtered off by using Millipore filter (Japan Millipore Limited, Type HA:0.45 μm) and the filtrate was neutralized by adding acetic acid (0.4 ml). The precipitating crystals were collected by filtration, washed with ice-water, methanol and ether in turn and then dried at 70° C. under reduced pressure to give the captioned compound (0.826 g) as colorless crystals.

IR (KBr): 3340, 3200, 2930, 1680, 1660, 1610, 1540, 1455, 1400, 1300, 1250, 1140 cm$^{-1}$.

$^1$H-NMR (Me2SO-d$_6$) δ: 1.78-1.97(3H,m), 1.98-2.16(1H,m), 2.33(2H,t,J=7.4 Hz), 2.71(2H,t,J=7.6 Hz), 2.85(2H,t,J=7.6 Hz), 4.26-4.39(1H,m), 5.51(2H), 6.14(2H, s), 6.45(1H,s), 6.88(1H,d,J=3.6 Hz), 7,68(1H,d,J=3.6 Hz), 8.45(1H,d,J=7.6 Hz), 10,49(1H,s)

EXAMPLE 4

Preparation of tert-butyl 5- [3-(2,4-diamino-6hydroxypyrrolo[2,3-d]pyrimidin-5-yl)propyl]-2thiophenecarboxylate In an atmosphere of argon gas, a solution of the compound (3.39 g) of Reference Example 10 in tert-butanol (30 ml) was added to a solution of potassium tert-butoxide (2.35 g) and guanidine hydrochloride (1.07 g) in tert-butanol (10 ml). The mixture was refluxed for 20 hrs. After cooling, the reaction mixture was added to 1N-potassium hydrogen sulfate solution (ca. 10 ml) at 0° C. and adjusted to pH 9.0. The mixture was extracted with a mixed solvent of tetrahydrofuran-chloroform and distilled under reduced pressure to remove the solvent. The resultant residue was purified by silica gel column chromatography (developing solvent: dichloromethane: ethanol=15:1→dichloromethane separated from conc. ammonia solution: ethanol=15:1 ) to give the captioned compound (2.29 g) .

IR (KBr): 3430, 3360, 1710, 1630, 1535, 1432 cm$^{-1}$.

$^1$H-NMR (Me$_2$SO-d$_6$ ) δ: 1.21-1.56(2H,m), 1.55 (9H,s) 1.69-2.02(2H,m), 2.81(2H,t,J=7 Hz), 3.29 (1H,t,J=6 Hz), 5.80(2H, br.s), 5.95(2H,br.s), 6.79(1H,d,J=3.6 Hz), 7.49(1H,d,J=3.6 Hz), 10.4(1H,s).

EXAMPLE 5

Preparation of tert-butyl 5-[3-(2,4-diamino-7Hpyrrolo[2,3-d]pyrimidin-5-yl)propyl]-2-thiophenecarboxylate A solution of the compound (575 mg) of Example 4 in tetrahydrofuran (6 ml) was added to a solution of borane-tetrahydrofuran complex (7.5 mmol) in tetrahydrofuran (7.5 ml) at 0° C., followed by stirring for 4.5 hrs. To the reaction mixture was added a mixed solution of acetic acid and methanol (1:1, 6 ml), and the mixture was stirred for 15 hrs at room temperature. The solvent was distilled off under reduced pressure, and the resultant residue was purified by silica gel column chromatography (developing solvent: dichloromethane:ethanol=100:6→8:1) to give the captioned compound (275 mg).

IR (KBr): 3335, 3180, 2975, 2935, 1710, 1540, 1287, 1163, 1110 cm$^{-1}$, $^1$H-NMR (Me2SO-d$_6$) δ: 1.56(9H,s), 1.75-1.92 (2H,m), 2.71(2H,t,J=7 Hz), 2.90(2H,t,J=7 Hz), 5.56(2H,br.s), 6.12(2H, br.s), 6.46(1H,s), 6.86 (1H,d,J=3.6 Hz), 7.51 (1H,d,J=3.6 Hz), 10.52 (1H,s).

EXAMPLE 6

Preparation of tert-butyl 5-[3-(2,4-diamino6,7-dihydro-5H-pyrrolo[2,3-d]pyrimidin-5-yl)propyl]-2thiophenecarboxylate A solution of borane-tetrahydrofuran complex (16.8 mmol) in tetrahydrofuran (10 ml) was added to a solution of the compound (437 mg) of Example 4 in tetrafuran (10 ml). The mixture was refluxed for 4 hrs. After cooling, the reaction mixture was poured into ice-water, adjusted with 1N hydrochloric acid to pH 2, then adjusted with 2N-potassium carbonate solution to pH 10.5 and stirred vigorously for 5 mins. The mixture was extracted with a mixed solvent of tetrahydrofuran and chloroform. The solvent was distilled off under reduced pressure, and the resultant residue was purified by silica gel column chromatography (developing solvent: dichloromethane: ethanol=30:1→15:1, dichloromethane separated from conc. ammonia: ethanol=20:1) to give the captioned compound (131 mg).

IR (KBr): 3375, 3325, 3190, 2970, 2930, 1712, 1538 cm$^{-1}$.

$^1$H-NMR (Me$^2$SO-d$_6$) δ: 1.21-1.69(4H,m), 1.56 (9H,s), 2.85(2H,t,J=7 Hz), 3.01(1H,dd,J=10 Hz,3 Hz), 3.03(1H,t, J=7.8 Hz) , 3.39(1H,t, J=10 Hz), 5.36(2H,br.s), 5.42(2H,br.s), 5.92(1H, s), 6.84(1H,d,J=3.6 Hz), 7.51 (1H,d,J=3.6 Hz )

EXAMPLE 7

Preparation of diethyl N-[5-[3-(2,4-diamino-6,7-dihydro-5H-pyrrolo[2,3-d]pyrimidin-5-yl)propyl]-2-thenoyl]-L-glutamate A solution of the compound (9.55 mg) of Example 6 in trifluoroacetic acid (1 ml) was stirred for 3 hrs at room temperature. The mixture was distilled under reduced pressure to remove the solvent and dried at 70° C. under reduced pressure. To a solution of residue and diethyl L-glutamate (304 mg) in the dimethylformamide (2 ml) was added a solution of diphenylphosphorylazide (350 mg) in dimethylformamide (1.5 ml) at 0° C. and then added dropwise a solution of triethylamine (180 mg) in dimethylfomamide (1.5 ml) at the same temperature. The mixture was stirred at 0° C. for 30 mins and then at room temperature for 78 hrs. The solvent was distilled off under reduced pressure, and the resultant residue was purified by silica gel column chromatography (developing solvent: dichloromethane separated from conc. ammonia dichloromethane→separated from conc. ammonia: ethanol=40: 1→30:1) to give the captioned compound (92 mg).

IR (KBr): 3350, 2990, 2945,1740, 1540, 1508, 1438 cm$^{-1}$.

$^1$H-NMR (Me$_2$SO-d$_6$) δ: 1.17(3H,t,J=7 Hz), 1.19 (3H,t,J=7 Hz), 1.25-1.42 (1H,m), 1.47-1.70(3H,m), 1.92-2.20(2H,m), 2.44(2H, t,J=7.4 Hz), 2,84(2H,br.t), 3.03(1H,dd,J=10 Hz,3 Hz), 3.05(1H,t,J=7.8 Hz), 3.41 (1H,t,J=10 Hz), 4.04(2H,q, J=7 Hz), 4.11(2H,q,J=7 Hz), 4.36-4.49(1H,m), 5.29(2H, br.s), 5.36(2H,br.s), 5.87 (1H,s), 6.83(1H,d,J=3.6 Hz), 7.49(1H,d,J=3.6 Hz), 8.63 (1H,d,J=7.8Hz).

EXAMPLE 8

Preparation of N-[5-[3-(2,4-diamino-6,7-dihydro5H-pyrrolo[2,3-d]pyrimidin-5-yl)propyl]-2-thenoyl]-L-glutamic acid The compound (62 mg) of Example 7 was dissolved in a mixed solvent of tetrahydrofuran and water (1:1, 2.5 ml). 1N Sodium hydroxide solution (0.37 ml) was added to this solution. The mixture was stirred at room temperature for 1.5 hrs and concentrated under reduced pressure to a volume of 1 ml. The resultant insoluble substance was filtered off by using millipore filter. The filtrate was cooled in an ice-bath and neutralized by adding acetic acid (0.1 ml). The precipitating crystals were collected by filtration, washed fully with water and then dried at 70° C. to give the captioned compound (49 mg) as white crystals.

IR (KBr): 3700-3350, 3215, 1690-1620, 1540 cm$^{-1}$.

$^1$H-NMR (Me$_2$SO-d$_6$+D$_2$O) δ: 1.26-1.77(4H,m), 1.89-2.16(2H,m), 2.31(2H,t,J=7 Hz), 2.85(2H,br.t), 3.13-3.28(2H,m), 3.56(1H, t,J=10 Hz), 4.15-4.40 (1H,m), 6.81(1H,d,J=3.6 Hz), 7.46(1H,d,J=3.6Hz).

EXAMPLE 9

Preparation of methyl 7-[2,4-diamino-6-hydroxy-7Hpyrrolo[2,3-d]pyrimidin-5-yl]heptanoate The compound (4.91 g) of Reference Example 12 was subjected to the same method as in Example 4 to give the captioned compound (3.66 g).

IR (KBr): 3420, 3360, 2980, 2955, 1735, 1640, 1435, 1370, 1250 cm$^{-1}$.

$^1$H-NMR (Me$_2$SO-d$_6$+D$_2$O) δ: 1.15-2.06(10H,br., m), 2.29(2H,t,J=7 Hz), 3.31(1H,t,J=6 Hz), 3,75 (3H, s).

EXAMPLE 10

Preparation of methyl 7-[2,4-diamino-6,7-dihydro-5H-pyrrolo[2,3-d]pyrimidin-5-yl]heptanoate (A) and methyl 7-[2,4-diamino-7H-pyrrolo[2,3-d]pyrimidin-5-yl]heptanoate (B)

A solution of borane-tetrahydrofuran complex (60 mmol) in tetrahydrofuran (60 ml) was added to a suspension of the compound (3.08 g) of Example 9 in tetrahydrofuran (40 ml). The mixture was stirred for 10 mins and then at 10°-15° C. for 6.5 hrs. After cooling, a mixed solution of acetic acid and methanol (1:2, 90 ml) was added to the reaction mixture. The mixture was stirred at room temperature for 18 hrs, and the solvent was distilled off under reduced pressure. The resultant residue was purified by silica gel column chromatography (developing solvent: dichloromethane: ethanol containing 8% ammonia=33:1→25:1) to give the captioned compound (A;1.35 g) and the captioned compound (B;0.796 g).

The Captioned Compound (A)

IR (KBr): 3370, 3325, 3190, 2970, 1735, 1440, 1365 cm$^{-1}$.

$^1$H-NMR (Me$_2$SO-d$_6$+D$_2$O) δ: 1.10-1.97 (10H,br. ,m), 2.32(2H,t,J=7 Hz), 2,95 -3.10(2H,m), 3.38(1H, t,J=10 Hz), 3.72(3H,s)

The Captioned Compound (B)

IR (KBr): 3340, 3180, 2975, 2935 , 1735, 1445 , 1365 cm$^{-1}$.

$^1$H-NMR (Me$_2$SO-d$_6$+D$_2$O) δ: 1.08-2.01(8H,br. ,m), 2,30(2H,t,J=7 Hz), 2.72 (2H,t,J=7 Hz), 3.73(3H, s), 6.49(1H,s).

EXAMPLE 11

Preparation of diethyl N-[7-(2,4-diamino-6,7-dihydro-5H-pyrrolo[2,3-d]pyrimidin-5-yl)heptanoyl]-L-glutamate A solution of 50% aqueous methanol (40 ml) and 1N sodium hydroxide (16 ml) were added to the compound (A) (1.18 g) of Example 10. The mixture was stirred at room temperature for 18 hrs, neutralized with 1N hydrochloric acid (16 ml), distilled under reduced pressure to remove the solvent and then dried at 80° C. In an atmosphere of argon gas, the entire amount of the residue and 1.44 g of diethyl L-glutamate hydrochloride were dissolved in dimethylformamide (40 ml). A solution of diethyl phosphorocyanidate (DEPC) (685 mg) in dimethylformamide (5 ml) was added to the above solution at 0° C., followed by stirring for 15 mins. A solution of triethylamine (1.42 g) in dimethylformamide (5 ml) was added dropwise to the solution at the same temperature. The reaction mixture was stirred at 0° C. for 30 mins and then at room temperature for 4 hrs and filtered to remove the resultant insoluble substance. The solvent was distilled off under reduced pressure, and the residue was purified by silica gel chromatography (developing solvent: dichloromethane:ethanol containing 8% ammonia solution=33:1→25:1) to give the captioned compound (1.28 g).

IR (KBr): 3350, 2985, 2945, 1740, 1440, 1365 cm$^{-1}$.

$^1$H-NMR (Me$_2$SO-d$_6$+D$_2$O) δ: 1.09-1.99(10H,br.,m), 1.18(3H,t,J=7 Hz), 1.20 (3H,t,J=7 Hz), 2.02-2.25 (2H,m), 2.34(2H,br.,t), 2.45(2H,t,J=7 Hz), 3.0-3.15(2H,m), 3.39(1H,t, J=10 Hz), 4.05(2H,q,$^J$=7 Hz), 4.12(2H,q,J=7 Hz), 4.35-4.50(1H,m).

EXAMPLE 12

Preparation of N-[7-(2,4-diamino-6,7-di-hydro-5H-pyrrolo[2,3-d]pyrimidin-5-yl)heptanoyl]-L-glutamic acid The compound (1.16 g) of Example 11 was reacted in the same method as in Example 8 to give the captioned compound (868 mg).

IR (KBr): 3650-3300, 3215, 2990, 2950, 1690-1625, 1435, 1370 cm$^{-1}$.

$^1$H-NMR (Me$_2$SO-d$_6$+D$_2$O) δ: 1.12-1.95(10H,br.,m), 1.97-2.19(2H,m), 2.32 (2H,t,J=7 Hz), 2.43(2H, t,J=7 Hz), 3.12-3.27(2H, m), 3.48(1H,t,J=10 Hz), 4.15-4.40(1H,m)

EXAMPLE 13

Preparation of diethyl
N-[7-(2,4-diamino-7-H-pyrrolo[2,3-d]pyrimidin-5-yl)heptanoyl]-L-glutamate The compound (B) (583 mg) of Example 10 was treated in the same method as in Example 11 to give the captioned compound (490 mg).

IR (KBr): 3330, 3160, 2975, 2935, 1735, 1443, 1369 cm$^{-1}$.

$^1$H-NMR (Me$_2$SO-d$_6$+D$_2$O) δ: 1.07–2.0(8H,br.,m), 1.17(3H,t,J=7 Hz), 1.20(3H,t,J=7 Hz), 2.01–2.20(2H,m), 2,31 (2H,t,J=7 Hz), 2,43(2H, t,J=7 Hz), 2,73(2H,t,J=7 Hz), 4.04(2H,q,J=7 Hz), 4.11(2H,q,J=7 Hz), 4.32–4.49(1H,m), 6.47(1H,s).

EXAMPLE 14

Preparation of
N-[7-(2,4-diamino-7H-pyrrolo[2,3-d]pyrimidin-5-yl)heptanoyl]-L-glutamic acid The compound (463 mg) of Example 13 was reacted in the same method as in Example 8 to give the captioned compound (334 mg).

IR (KBr): 3340, 3200, 2975, 2960, 1660–1630, 1445, 1370 cm$^{-1}$.

$^1$H-NMR (Me$_2$SO-d$_6$+D$_2$O) δ: 1.09–1.90(8H,br.,m), 1.97–2.21(2H,m), 2.30 (2H,t,J=7 Hz), 2.41(2H, t,J=7 Hz), 2.70(2H,t,J=7 Hz), 4.21–4.48(1H,m), 6.51(1H,s).

EXAMPLE 15

Preparation of methyl
5-[3-(2-amino-4-hydroxy-6,7-dihydro-5H-pyrrolo[2,3-d]pyrimidin-5-yl)propyl]-2-thiophencarboxylate A solution of 0.21N hydrobromic acid in dichloromethane (78.3 ml) was added to a solution of the compound (0.67 g) obtained in Reference Example 14 in anhydrous tetrahydrofuran (31.5 ml). The mixture was stirred at room temperature for 20 hrs. To the mixture was added three volumes of n-hexane. The precipitating substances were collected by filtration to give hydrobromide (0.60 g) of the captioned compound.

IR (KBr): 3290, 3030, 2950, 1720, 1690, 1680, 1540, 1480, 1350, 1275, 1100, 1035, 760 cm$^{-1}$.

$^1$H-NMR (Me$_2$SO-d$_6$) δ: 1,38–1,85(4H,broad), 2.79 (2H,t,J=7 Hz), 3.05–3.35(2H, m), 3.49–3.75(1H,m), 3.86 (3H,s), 6.82(1H,d,J=3.6 Hz), 7.53 (1H,d,J=3.6 Hz).

EXAMPLE 16

Preparation of diethyl
N-[5-[3-(2-amino-4-hydroxy-6,7-dihydro-5}t-pyrrolo[2,3-d]pyrimidin-5-yl)propyl]-2thenoyl]-L-glutamate 0.1N Sodium hydroxide solution (120 ml) was added to a suspension of the compound (1.49 g) obtained in Example 15 in tetrahydrofuran (60 ml), followed stirring at room temperature for 21 hrs. Then the mixture was neutralized with 0.1N hydrochloric acid (60 ml) and concentrated to dryness under reduced pressure. The residue was suspended in dry dimethylformamide (112.5 ml). To the solution were added diethyl L-glutamate hydrochloride (2.88 g), diphenylphosphorylazide (1.295 ml) and triethylamine (2.52 ml) under ice-cooling. The temperature of the mixture was raised to room temperature and allowed to stand for 63 hrs. The resultant precipitate was removed by filtration, and the filtrate was concentrated to dryness under reduced pressure. The residue was purified by silica gel column chromatography (developing solvent: ethanol containing 6.9% ammonia:chloroform=1:20→1:10) to give the captioned compound (1.10 g).

IR (KBr): 3330, 2930, 1740, 1670, 1640, 1540, 1440, 1375, 1300, 1200, 1095, 1020 cm$^{-1}$.

$^1$H-NMR (CDCl$_3$/CD$_3$OD) δ: 1.21(3H,t,J=7 Hz), 1.28 (3H,t,J=7 Hz), 1.46–1.82 (4H,m), 2.02–2.35(2H,m), 2.37–2.51(2H,m), 2.79(2H, t,J=7 Hz), 3.11–3.36(2H, m), 3.52–3.77(1H,m), 3.97–4.34(4H,q×2,J=7 Hz), 4.61–4.86(1H,m), 6.78(1H, d,J=3.6 Hz), 7.48(1H,d, J=3.6 Hz)

EXAMPLE 17

Preparation of
N-[5-[3-(2-amino-4-hydroxy-6,7-dihydro-5H-pyrrolo[2,3-d]pyrimidin-5-yl)propyl]-2thenoyl]-L-glutamic acid 1N Sodium hydroxide solution (5.34 ml) was added to a solution of the compound (0.90 g) of Example 16 in tetrahydrofuran and water (2:1, 60 ml). The mixture was stirred at room temperature for 2.5 hrs. Tetrahydrofuran was distilled off and a small amount of insoluble substance was removed by filtration. To the filtrate was added acetic acid (0.5 ml). The resultant precipitate was collected by filtration, washed with water and dried to give the captioned compound (0.75 g).

IR (KBr): 3340, 2930, 1690, 1630, 1540, 1440, 1300, 1080, 850 cm$^{-1}$.

$^1$H-NMR (Me2SO-d6+D20) δ: 1.19–1.81(4H,m), 1.86–2.18(2H,m), 2.22–2.41 (2H,m), 2.52–2.85(2H, m), 2.87–3.21(2H,m), 3.32–3.64(1H,m), 4.22–4.53(1H,m), 6.77(1H,d, J=3.6 Hz), 7.51(1H,d,J=3.6 Hz)

EXAMPLE 18

Preparation of diethyl
N-[5-[3-(2-amino-4-hydroxy7H-pyrrolo[2,3-d]pyrimidin-5-yl)propyl]-2-thenoyl]-L-glutamate To a solution of the compound (150 mg) of Example 16 in ethanol (22.5 ml) were added 10% Pd-C (450 mg;Engelhard's product) and acetic acid (2 drops). The mixture was stirred vigorously at room temperature for 62.5 hrs. The catalyst was removed by filtration, and the filtrate was concentrated to dryness. The residue was purified by silica gel column chromatography (developing solvent: chloroform containing 5% ethanol) to give the captioned compound (40 mg).

IR (KBr ): 3340, 2940, 1740, 1680, 1670, 1540, 1440, 1380, 1340, 1210, 1100, 1020, 860 cm$^{-1}$.

$^1$H-NMR (CDCl$_3$) δ: 1.20(3H,t,J=7 Hz), 1.27(3H, t,J=7 Hz), 1.86–2.37(4H,m), 2.41–2.58(2H,m), 2.61–2.88 (4H,m), 3.95–4.37(4H,q×2, J=7 Hz), 4.55–4.88(1H,m), 6.38(1H,s), 6.79(1H,d,J=3.6 Hz), 7.52(1H,d,J=3.6 Hz)

EXAMPLE 19

Preparation of N- [5- [3-(2-amino-4-hydroxy-7H-pyrrolo[2,3-d ] pyrimidin- 5-yl ) propyl ] - 2-thenoyl ] -L-glutamic acid The compound (31 mg) of Example 18 was dissolved in a mixed solvent of tetrahydrofuran and water (1:1, 2.4 ml). To the solution was added 1N sodium hydroxide solution (0.18 ml), followed by stirring at room temperature for 2.5 hrs. The mixture was distilled, and to the residue was added acetic acid (0.015 ml) under ice-cooling. The mixture was stirred, and then the resultant precipitates were collected by filtration and dried to give the captioned compound (21 mg).

IR (KBr ): 3400, 3300, 2950, 1700, 1650, 1540, 1510, 1400, 1340, 1240, 1080, 1020 cm$^{-1}$.

$^1$H-NMR (Me$_2$SO-d$_{6+D_2O}$) δ: 1.81–2.17(4H,m), 2.22–2.42(2H,m), 2.55–2.86 (4H,m), 4.26–4.55(1H, m), 6.35(1H,s), 6.81 (1H,d,J=3.6 Hz), 7.56 (1H,d,J=3.6 Hz).

The following compounds can be prepared in a similar manner to the above Examples.

(1) N-[5-[3-(2,4-diamino-6,7-dihydro-5H-pyrrolo[2,3-d]pyrimidin-5-yl)propyl]-2-thenoyl-L-glutamic acid,
(2) N-[5-[2-(2,4-diamino-6,7-dihydro-5H-pyrrolo[2,3-d]pyrimidin-5-yl)ethyl]-2-thenoyl]-L-glutamic acid,
(3) N-[5-[2-(2,4-diamino-7H-pyrrolo[2,3-d]pyrimidin-5-yl)ethyl]-2-thenoyl]glutamic acid,
(4) N-[5-[4-(2,4-diamino-6,7-dihydro-5H-pyrrolo[2,3-d]pyrimidin-5-yl)butyl]-2-thenoyl-L-glutamic acid,
(5) N-[5-[4-(2,4-diamino-7H-pyrrolo[2,3-d]pyrimidin-5yl)butyl]-2-thenoyl]-L-glutamic acid,
(6) N-[5-[3-(2,4-diamino-6,7-dihydro-5H-pyrrolo[2,3-d]pyrimidin-5-yl)-1-methylpropyl]-2-thenoyl]-L-glutamic acid,
(7) N-[5-[3-(2,4-diamino-7H-pyrrolo[2,3-d]pyrimidin-5-yl)-1-methylpropyl]-2-thenoyl]-L-glutamic acid,
(8) N-[5-[3-(2,4-diamino-6,7-dihydro-5H-pyrrolo[2,3-d]pyrimidin-5-yl)-1,1-dimethylpropyl]-2-thenoyl]-L-glutamic acid,
(9) N-[5-[3-(2,4-diamino-7H-pyrrolo[2,3-d]pyrimidin-5-yl)-1,1-dimethylpropyl]-2-thenoyl]-L-glutamic acid,
(10) N-[5-[3-(2,4-diamino-6,7-dihydro-5H-pyrrolo[2,3-d]pyrimidin-5-yl)-1-ethylpropyl]-2-thenoyl]-L-glutamic acid,
(11) N-[5-[3[(2,4-diamino-7H-pyrrolo[2,3-d]pyrimidin-5-yl)-1-ethylpropyl]-2-thenoyl]-L-glutamic acid,
(12) N-{5-{3-(2,4-diamino-6,7-dihydro-5H-pyrrolo[2,3-d]pyrimidin-5-yl)propyl]-2-pyridinecarbonyl]-L-glutamic acid,
(13) N-[5-[3-(2,4-diamino-7H-pyrrolo[2,3-d]pyrimidin-5yl)propyl]-2-pyridinecarbonyl]-L-glutamic acid,
(14) N-[4-[3-(2,4-diamino-6,7-dihydro-5H-pyrrolo[2,3-d]pyrimidin-5-yl)propyl]cyclohexanecarbonyl]-L-glutamic acid,
(15) N-[4-[3-(2,4-diamino-7H-pyrrolo[2,3-d]pyrimidin-5yl)propyl]cyclohexanecarbonyl]-L-glutamic acid,
(16) N-[5-(2,4-diamino-6,7-dihydro-5H-pyrrolo[2,3-d]pyrimidin-5-yl)pentanoyl]-L-glutamic acid,
(17) N-[5-(2,4-diamino-7H-pyrrolo[2,3-d]pyrimidin-5-yl) pentanoyl]-L-glutamic acid,
(18) N-[6-(2,4-diamino-6,7-dihydro-5H-pyrrolo[2,3-d]pyrimidin-5-yl)hexanoyl]-L-glutamic acid,
(19) N-[6-(2,4-diamino-7H-pyrrolo[2,3-d]pyrimidin-5-yl) hexanoyl]-L-glutamic acid,
(20) N-[5-[3-(2,4-diamino-6,7-dihydro-5H-pyrrolo[2,3-d]pyrimidin-5-yl)propyl]thiazole-2-carbonyl]-L-glutamic acid,
(21) N-[5-[3,(2,4-diamino-7H-pyrrolo[2,3-d]pyrimidin-5-yl)propyl]thiazole-2-carbonyl]-L-glutamic acid,
(22) N-[5-[3-(2-amino-4-hydroxy-6,7-dihydro-5H-pyrrolo [2,3-d]pyrimidin-5-yl)propyl]-2-thenoyl]-glutamic acid,
(23) N-[5-[3-(2-amino-4-hydroxy-7H-pyrrolo[2,3-d]pyrimidin -5-yl)propyl]-2-thenoyl]-L-glutamic acid,
(24) N-[5-[2-(2-amino-4-hydroxy-6,7-dihydro-5H-pyrrolo [2,3-d]pyrimidin-5-yl)ethyl]-2-thenoyl]-L-glutamic acid,
(25) N-[5-[2-(2-amino-4-pydroxy-7H-pyrrolo[2,3-d]pyrimidin-5-yl)ethyl]-2-thenoyl]-L-glutamic acid,
(26) N-[5-[3-(2-amino-4-hydroxy-6,7-dihydro-5H-pyrrolo [2,3-d]pyrimidin-5-yl)-1-methylpropyl]-2-thenoyl]-L-glutamic acid,
(27) N-[5-[3-(2-amino-4-hydroxy-7H-pyrrolo[2,3-d]pyrimidin- 5-yl)-1-methylpropyl]-2-thenoyl-L-glutamic acid,
(28) N-[5-[3-(2-amino-4-hydroxy-6,7-dihydro-5H-pyrrolo [2,3-d]pyrimidin-5-yl)propyl]-2-pyridinecarbonyl]-L-glutamic acid,
(29) N-[5-[3-(2-amino-4-hydroxy-7H-pyrrolo[2,3-d]pyrimidin-5-yl)propyl]-2-pyridinecarbonyl]-L-glutamic acid,
(30) N-[6-(2-amino-4-hydroxy-6,7-dihydro-5H-pyrrolo [2,3-d]pyrimidin-5-yl)hexanoyl]-L-glutamic acid,
(31) N-[6-(2-amino-4-hydroxy-7H-pyrrolo[2,3-d]pyrimidin-5-yl)hexanoyl]-L-glutamic acid,
(32) N-[5-[3-(2-amino-4-hydroxy-6,7-dihydro-5H-pyrrolo [2,3-d]pyrimidin-5-yl(propyl]thiazole-2-carbonyl]-L-glutamic acid and
(33) N-[5-[3-(2-amino-4-hydroxy-7H-pyrrolo[2,3-d]pyrimidin-5-yl)propyl]thiazole-2-carbonyl]-L-glutamic acid.

The object compounds (I) of this invention and their salts are novel and possess an excellent antitumor activity, and accordingly can be presented as a safe and new antitumor agent for warm-blooded animals, especially in the treatment of solid tumors such as KB, B$^{16}$ malanoma or the like.

What we claim is:

1. A compound of the formula (1):

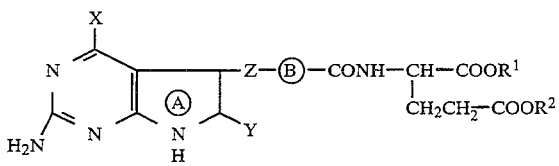

wherein the ring Ⓐ is a pyrrole ring which may be hydrogenated, X is an amino group, a hydroxyl group or a mercapto group, Y is a hydroxyl group, —COOR$^1$ and —COOR$^2$ may be the same or different and are a carboxyl group which may be esterified by a C$_{1-5}$ lower alkyl group, benzyl, nitrobenzyl, methoxybenzyl, phenyl, nitrophenyl, phenyl, nitrophenyl or methoxyphenyl, —Ⓑ— is a thiophen-(2,4-, 2,5- or 3,4-)ylene which may have 1 or 2 substituents selected from the group consisting of a halogen, methoxy, dimethylamino, methyl and trifluoromethyl and Z is a straight C$_{2-4}$ divalent group which may be substituted with 1 or 2 groups selected from the group consisting of a C$_{1-3}$ alkyl, C$_{2-3}$ alkenyl, C$_{2-3}$ alkynyl, cyclopropyl, fluoro, hydroxy, oxo, methoxy, dimethylamino, diethylamino, trifluoromethyl, formyl, hydroxymethyl, 2-hydroxyethyl, methoxymethyl and 2-methoxyethyl, or its pharmaceutically acceptable salt.

2. A compound of claim 1 in which the Ⓐ is a pyrrole ring, X is an amino group.

3. A compound of claim 1 in which the Ⓐ ring is a pyrrole ring, X is an amino group, —Ⓑ— is a thiophen-(2,4-)ylene group, COOR$^1$ and COOR$^2$ are a carboxyl group and Z is a propylene group.

4. A pharmaceutical composition for treating human epidermoid carcinoma KB comprising an effective amount of a compound (I) of claim 1 or its pharmaceutically acceptable salt together with a pharmaceutically acceptable carrier or diluent.

5. A method of treating human epidermoid carcinoma KB comprising administering to a patient in need thereof an effective amount of a compound (I) of claim 1 or its pharmaceutically acceptable salt together with a pharmaceutically acceptable carrier or diluent.

* * * * *